United States Patent [19]

Klawitter

[11] 4,451,937

[45] Jun. 5, 1984

[54] HEART VALVE HAVING EAR GUIDED OCCLUDERS

[75] Inventor: Jerome J. Klawitter, Austin, Tex.

[73] Assignee: Hemex, Inc., Austin, Tex.

[21] Appl. No.: 346,722

[22] Filed: Feb. 8, 1982

[51] Int. Cl.³ .............................................. A61F 1/22
[52] U.S. Cl. ..................................... 3/1.5; 137/512.1; 137/527; 137/527.8
[58] Field of Search ................... 3/1.5; 137/512.1, 527, 137/527.8

[56] References Cited

U.S. PATENT DOCUMENTS

| | | | |
|---|---|---|---|
| 4,078,268 | 3/1978 | Possis | 3/1.5 |
| 4,159,543 | 7/1979 | Carpentier | 3/1.5 |
| 4,178,638 | 12/1979 | Meyer | 3/1.5 |
| 4,240,161 | 12/1980 | Huffstutler, Jr. et al. | 3/1.5 |
| 4,254,508 | 3/1981 | Bokros | 3/1.5 |
| 4,263,680 | 4/1981 | Reul et al. | 3/1.5 |
| 4,306,319 | 12/1981 | Kaster | 3/1.5 |
| 4,363,142 | 12/1982 | Meyer | 3/1.5 |

Primary Examiner—Ronald L. Frinks
Attorney, Agent, or Firm—Fitch, Even, Tabin & Flannery

[57] ABSTRACT

Heart valve prostheses have annular valve bodies with central passageways and valve members supported for pivotal and translational movement between open and closed positions. The occluders, which may be either of a bileaflet or single occluder design, are supported within the bodies by pairs of ears extending from opposite locations to interengage with corresponding arcuate depressions to guide the occluders between their closed positions where they seat against upstream protuberances of the valve bodies and their open position where they are positioned between the upstream protuberances and downstream protuberances.

24 Claims, 19 Drawing Figures

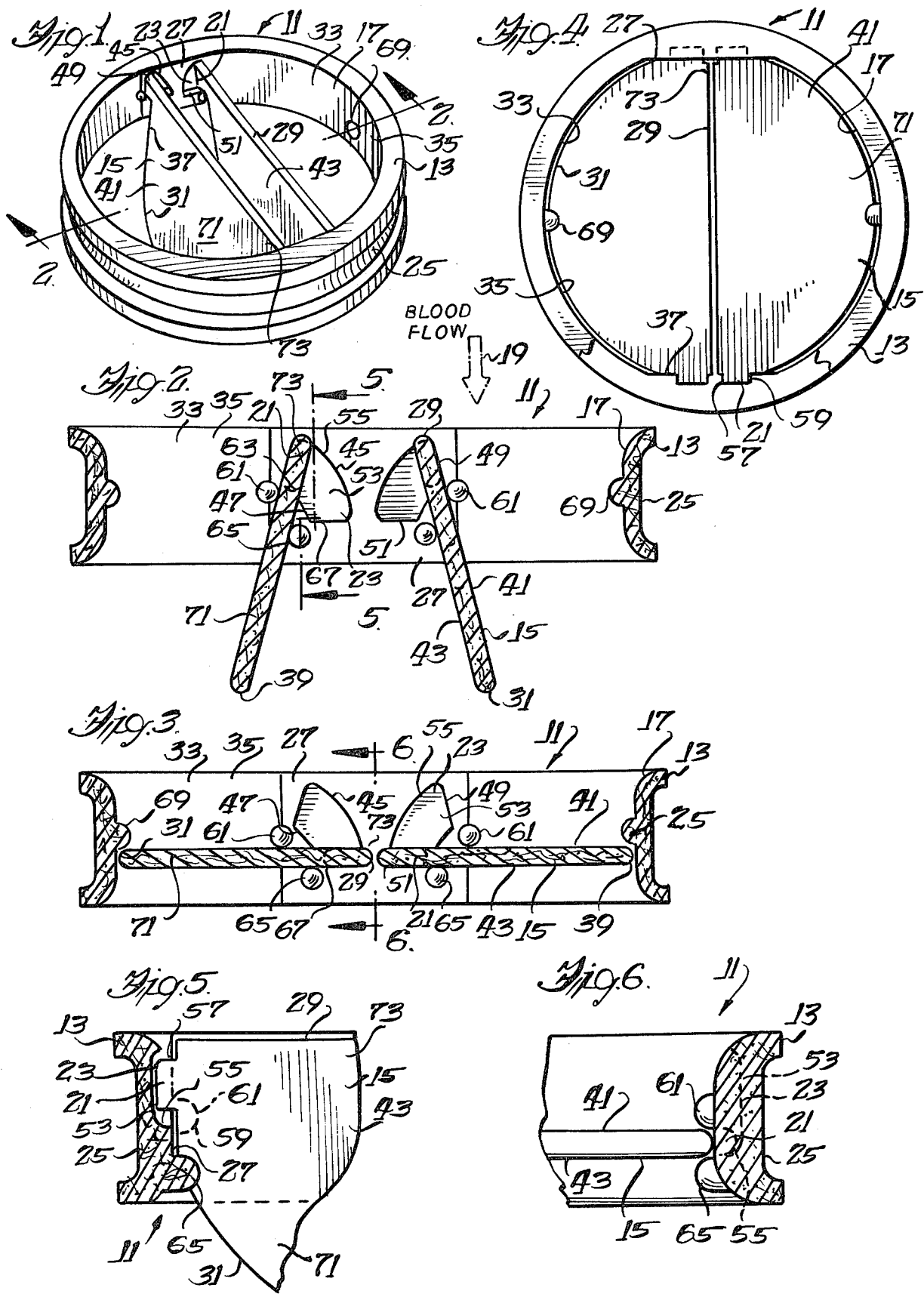

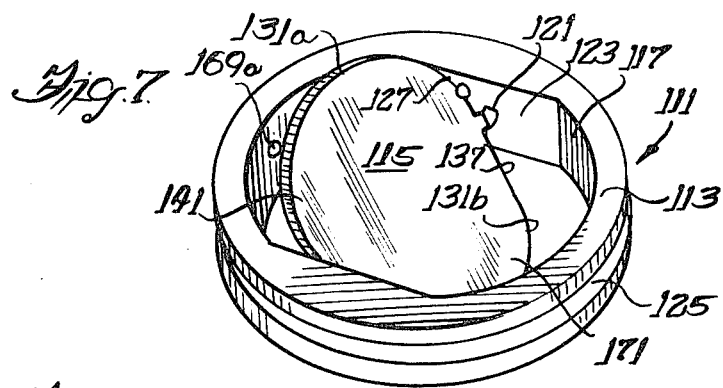
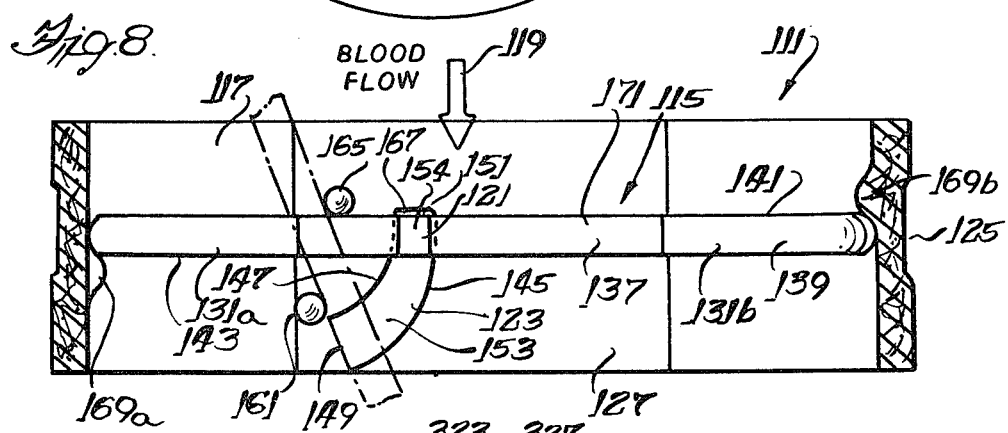
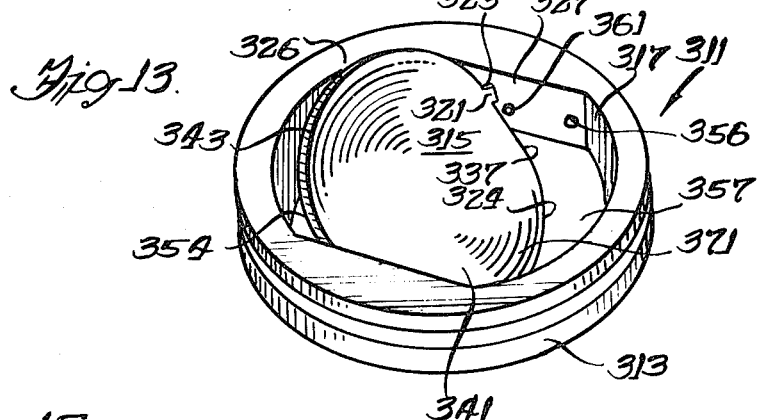
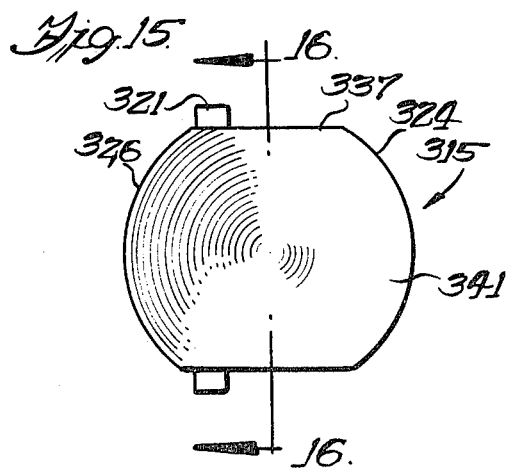
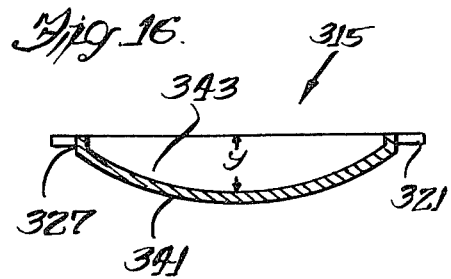

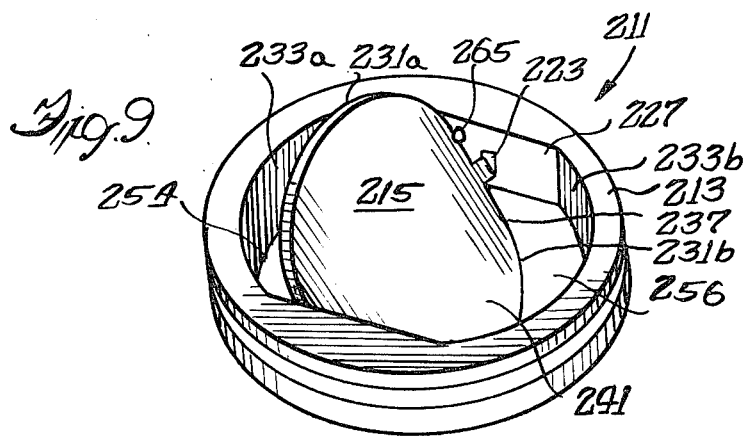
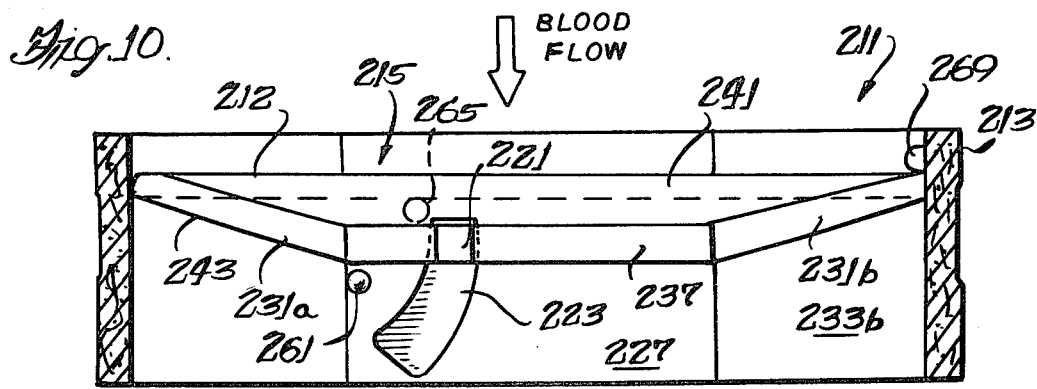
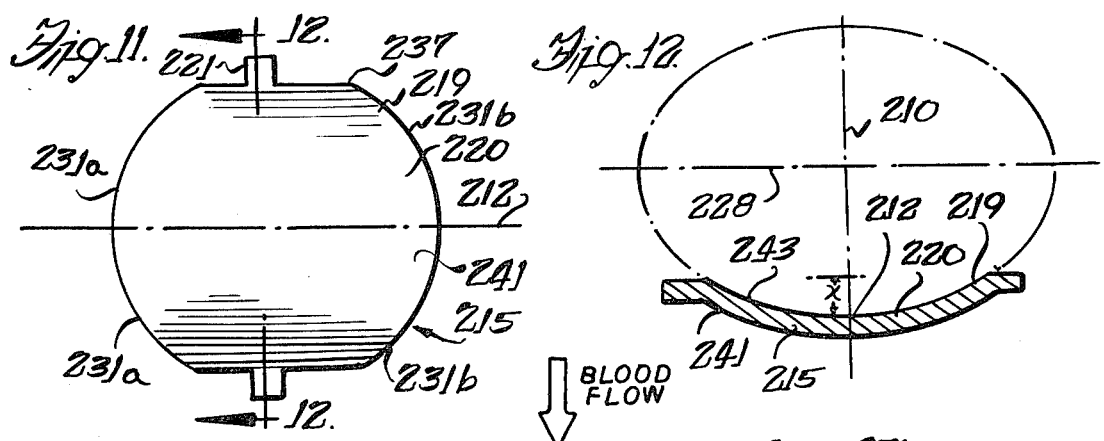
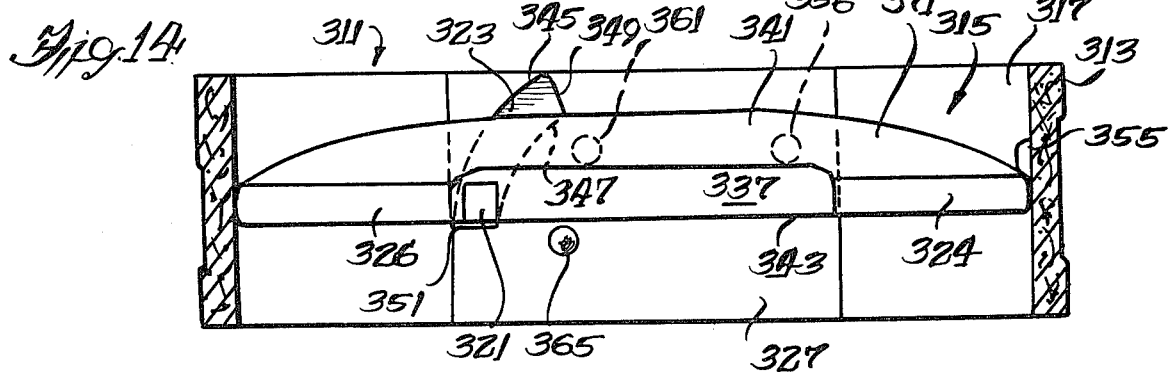

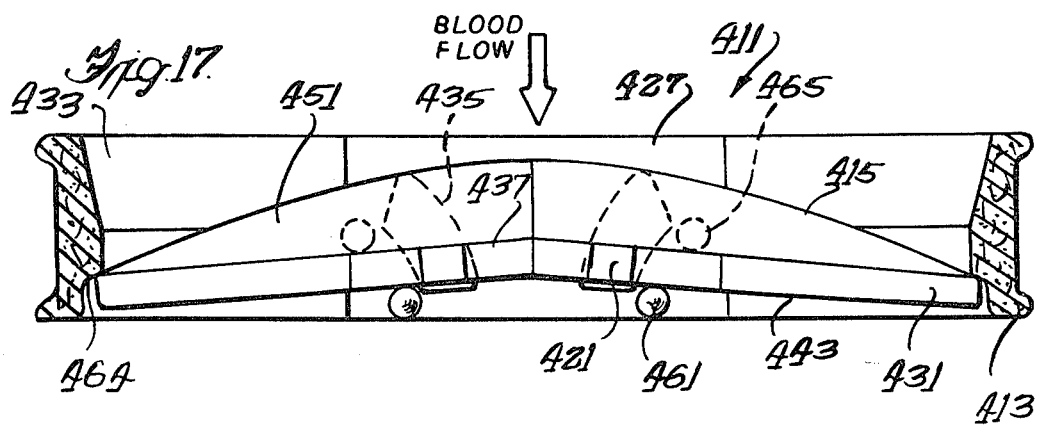
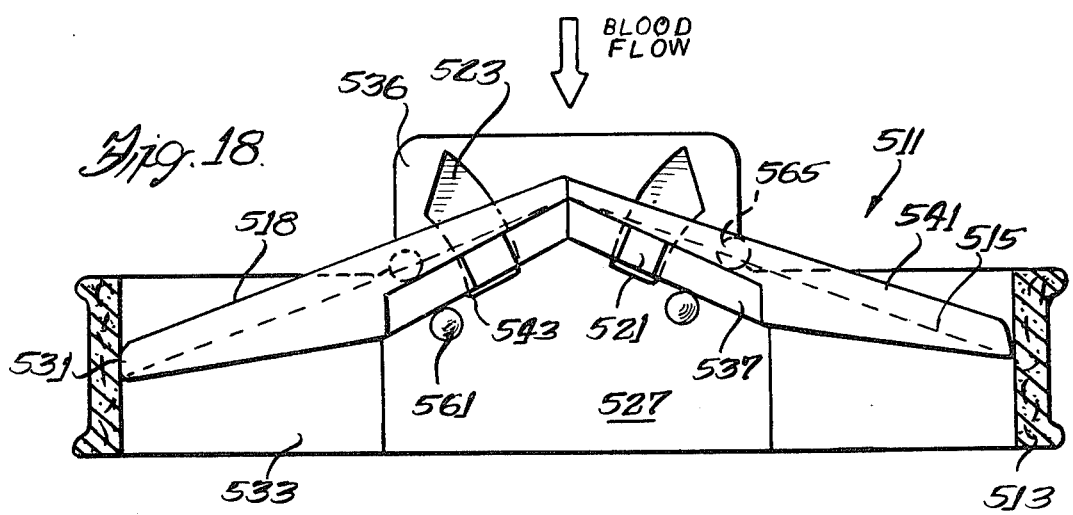
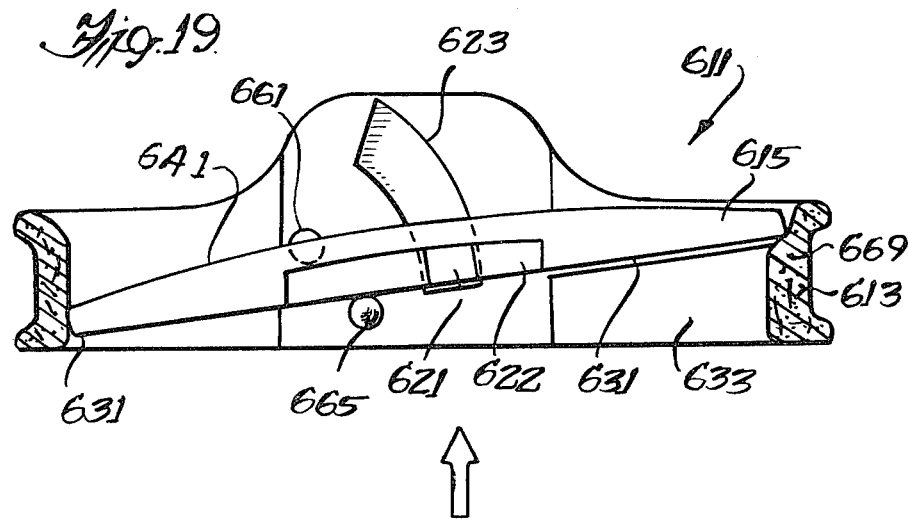

HEART VALVE HAVING EAR GUIDED OCCLUDERS

This invention relates to heart valve prostheses and more particularly to heart valves for permanent implantation into the human body.

BACKGROUND OF THE INVENTION

Bileaflet heart valves are described in U.S. Pat. No. 4,159,543 in which a pair of leaflets pivot along eccentric axes to open and close a blood passageway in response to the pumping of the heart. A single disc occluder which pivots between an open and closed position within an annular heart valve body is described in U.S. Pat. No. 3,546,711. The need continues for improved heart valves which are intended for permanent implantation into the human heart.

In its open position, a valve should provide a passageway which is large and which has good flow characteristics so that blood flows freely therethrough with a minimum of drag and eddy currents. A heart valve should be responsive to blood flow to quickly open during the pumping stroke of the heart and snap back quickly when the heart relaxes to prevent regurgitation of blood. The heart valve must, of course, be biocompatible and thromboresistant, and in this regard, it is important that all surfaces be well washed by blood to prevent stagnation which might lead to eventual clotting. The opening and closing of the valve should be sufficiently soft so as not to cause hemolysis (breaking of blood cells). The heart valve must withstand countless openings and closings, and particular care should be exercised so that the load-bearing surfaces such as the pivot points and stops do not wear out during the life of the patient. The above charactristics are desirably achieved with a simple design which not only simplifies manufacture, but reduces the amount of obstacles to efficient flood flow, reduces the nooks and crannies where blood may stagnate and reduces the quality control problems associated with complexity.

SUMMARY OF THE INVENTION

Generally annular heart valve bodies with central passageways therethrough have valve members which swing between closed positions to block blood flow through the passageways and open position to allow blood flow through the passageways. The valve membes are supported within the valve bodies by pairs of ears extending from opposite locations on their peripheries to interengage with arcuate depressions formed in the interior surfaces of the valve bodies. The depressions guide the valve members in pivotal and translational motion between their closed positions where their upstream surfaces seat against upstream protuberances associated with the depressions and their open positions where the valve members are positioned between the upstream protuberances and downstream protuberances associated with the depressions. Valve members may either be in the form of a single occluder or a pair of generally semicircular leaflets. A single occluder may have a convex-concave configuration, preferably with its convex surface facing upstream to equalize the flow of blood on each side of the occluder in its open position.

BRIEF DESCRIPTION OF THE DRAWINGS

FIG. 1 is a perspective view of the bileaflet heart valve embodying various features of the invention, shown in the open position.

FIG. 2 is a cross-sectional view, enlarged in size, taken along line 2—2 of FIG. 1.

FIG. 3 is a cross-sectional view similar to that of FIG. 2 showing the leaflets in the closed position.

FIG. 4 is a plan view, partially cut away, of the heart valve of FIG. 1 with the leaflets in the closed position.

FIG. 5 is an enlarged cross-sectional view taken along line 5—5 of FIG. 2.

FIG. 6 is an enlarged cross-sectional view taken along line 6—6 of FIG. 3.

FIG. 7 is perspective view of an alternative embodiment of a heart valve.

FIG. 8 is an enlarged cross-sectional view of the heart valve body of FIG. 7 shown with an elevation view of the occluder.

FIG. 9 is a perspective view of a further alternative embodiment of a heart valve.

FIG.10 is an enlarged cross-sectional view of the heart valve body of FIG. 9 shown with an elevation view of the occluder.

FIG. 11 is a plan view of the occluder of the heart valve of FIG. 9.

FIG. 12 is a cross-sectional view taken along line 12—12 of FIG. 11 (the occluder shown inverted relative to FIG. 10).

FIG. 13 is a perspective view of a still further alternative embodiment of a heart valve.

FIG. 14 is an enlarged cross-sectional view of the heart valve body of FIG. 13 shown with an elevation view of the occluder.

FIG. 15 is a plan view of the occluder of the heart valve of FIG. 13.

FIG. 16 is a cross-sectional view taken along line 16—16 of FIG. 15 (the occluder shown inverted relative to FIG. 14).

FIG. 17 is an illustration of a further alternative embodiment of a bileaflet heart valve including a cross-sectional view of the valve body and an elevation view of the leaflets within the valve body in the closed position.

FIG. 18 is an illustration of a further alternative embodiment of a bileaflet heart valve including a cross-sectional view of the valve body and an elevation view of the leaflets within the valve body in the closed position.

FIG. 19 is an illustration of a further alternative embodiment of a single occluder heart valve including a cross-sectional view of the valve body and an elevation view of the occluder within the valve body in its closed position.

DETAILED DESCRIPTION OF THE PREFERRED EMBODIMENT

Illustrated in FIG. 1 is a heart valve 11 which has an annular valve body or housing 13 which carries a pair of pivoting leaflets or valve members 15 which open and close to control the flow of blood through a central passageway 17 in the direction of the arrow 19 (FIG. 2). A pair of ears 21 extends from opposite ends of each leaflet 15 and interfits with a pair of opposed arcuate depressions 23 in the valve body 13, and the leaflet 15 is guided thereby as it swings between its open and closed positions. While the valve 11 can operate in any orientation and is not significantly affected by gravity, for ease of explanation, the valve is shown and described with the downstream end of the valve facing downward.

The valve body 13 is formed with a peripheral groove 25 about its exterior surface that accommodates a suturing ring (not shown) which may be any of the various types already well known in the art. The suturing ring, of course, facilitates the sewing or suturing of the heart valve 11 to the heart tissue. The passageway 17 through the valve body 13 is generally circular; however, a pair of diametrically opposed flat surfaces 27 in which depressions 23 are formed and several protuberances, hereinafter described, interrupt the otherwise circular configuration of the passageway.

The leaflets 15, as best seen in FIG. 3, are flat with a uniform thickness throughout. The leaflets 15 each are generally the shape of half of a circular disc, having straight minor edges 29 which lie closely adjacent each other in the closed position, as shown in FIGS. 3 and 4, and major edges 31 which are generally semicircular and porportioned to lie closely adjacent the arcuate portions 33 of the interior wall 35 in the closed position to block blood flow through the passageway 17. Straight segments 37 (FIG. 4) of the leaflet peripheries disposed between the major and minor edges 29, 31 interrupt the semicircular shape of the arcuate edge and are spaced apart slightly less than the distance between the opposed flat surfaces 27 of the interior wall 35 and alternately serve as load-bearing surfaces during the swinging movement of the leaflets 15. The flat surfaces 27 in the interior wall 35 and corresponding straight segments 37 of the leaflets 15 are provided so that those portions of the leaflet peripheries closely adjacent the centerline plane, i.e., the plane which runs through the valve body centerline perpendicular to the flat surfaces 27, do not bind in more restricted areas of the body 13 as they move away from the centerline plane during opening. The edges 39 (FIGS. 2 and 3) of the leaflets 15 are rounded between their upstream surfaces 41 and downstream surfaces 43 to eliminate sharp corners.

The interengagement of the ears 21 and the complementary depressions 23 serves both to retain the leaflets 15 in the valve body 13 and to define the movement of the leaflets therein. The ears 21, which extend from the straight segments 37 of the leaflets 15 into the depressions 23, have a generally rectangular configuration and are disposed closely adjacent the minor edges 29 of the leaflets 15. The depressions 23, as best seen in FIGS. 2 and 3, with which the ears 21 interengage, are generally the shape of arcuate troughs. The downstream edges 51, along which the ears 21 lie closely adjacent in the closed position of the leaflets 15, are preferably generally perpendicular to the centerline plane, and the arcuate edges 45, 47 extend upstream therefrom and curve away from the centerline plane. The upstream straight edges 49 along which the ears 21 lie closely adjacent in the open position of the leaflets 15, are angled from the centerline plane by about 10° to about 25° and the total angular movement of the ears in the depressions 23 is between about 65° about 80°.

The arcuate adjacent edge 45 and arcute remote edge 47 of each depression 23 are not parallel, but diverge toward their upstream ends so that the transverse dimension of each depression 23 increases in an upstream direction. While the length of each ear 21 is sufficient to substantially fill the space between the downstream ends of the adjacent and remote arcuate edges 45, 47 of the corresponding depression 23, the increasing upstream transverse dimension of each depression 23 assures that the depression is well washed by flowing blood to prevent stagnation and resulting clotting therein when the leaflets 15 are in non-closed positions.

The arcuate trough-shaped depressions 23 preferably have flat rear walls 53 (FIG. 2) along which the outer edges of the ears 21 locate as they swing between their open and closed positions and sidewalls 55 (FIG. 5). The arcuate edges 45, 47 of the depressions 23, which are substantially peripendicular to the flat surfaces 27 and to the rear walls 53, guide the corresponding adjacent edges 57 and remote edges 59 (FIG. 4) of the ears 21. Preferably, the depth of the ears 21 is less than the depth of the depressions 23 so that the leaflets 15 are laterally positioned by the flat surfaces 27 of the interior wall 35 and there is no contact between the rear walls 53 of the depressions 23 and the end surfaces of the ears.

The fully open position and fully closed position of the leaflets 15 are determined by bumps or protuberances which extend inward of the valve body 13. An upstream or upper bump or protuberance 61 associated with each depression is positioned slightly below (downstream of) and remote from the centerline plane relative to the corner 53 of the corresponding upstream and remote edges 49, 47, and a downstream or lower bump or protuberance 65 associated with each depression is positioned slightly below and remote from the centerline plane relative to the corner 67 of the downstream and remote edges 51, 47. A pair of midpoint protuberances 69 at diameterically opposite locations on the valve body 13 are positioned to contact the leaflets 15 at about the midpoints of their major arcuate edges 31.

In its closed position, each leaflet 15 seats with its upstream face or surface 41 abutting the corresponding upper protuberances 61 and midpoint protuberance 69 in a plane substantially perpendicular to the centerline plane. The upper protuberances 61 and midpoint protuberances 69 are so positioned that in the closed position, the downstream faces or surfaces 43 of the leaflets 15 lie closely adjacent to the corresponding lower protuberances 65. In its open position, each leaflet 15 is positioned with its upstream surface 41 abutting the upper protuberances 61 and its downstream surface 43 abutting the lower protuberances 65 and with its ears 21 abutting or lying closely adjacent the upstream straight edges 49.

The upper and lower protuberances 61, 65 serve as surfaces against which the leaflets 15 slide and pivot during closing and opening, respectively. Eccentric axes are defined between the contact points of the leaflets 15 and the corresponding pair of protuberances 61 or 65. The protuberances 61, 65 are positioned sufficiently close to the centerline plane so that a greater portion 71, i.e., the portion of greater area, of each leaflet is always on the side of its pivotal axis remote from the centerline plane.

For a valve 11 in the aortic position, during the pumping stroke of the heart, the force differential against the major portion 71 of each leaflet 15, resulting from blood pressure from the ventricle, swings each leaflet in its downstream direction with its major arcuate edge 31 moving in a wide arc. During opening, the ears 21 of the leaflets 15 are guided by the arcuate depressions 23 in a generally arcuate pathway as the downstream surfaces 43 slide and pivot against the lower protuberances 65. The arcuate depressions 23 are elongated and do not have a radius of curvature that coincides with the pivotal axes of the leaflets 15. Thus, during opening movement, there is a slight upstream translation of each leaflet 15, with each leaflet sliding as well as pivoting against the lower protuberances 65 so that the pivotal axis, defined by the contact of the lower protuberances and the downstream surface 43, continuously shifts toward the arcuate edge 31. The translational movement of the ears 21 within the depressions 23 and the relocation of the leaflets 15 relative to the protuberances 61, 65 results in a continual sliding of the contact surfaces which serves to prevent blood from stagnating in and clotting in the restricted areas in the depressions and around the protuberances. Furthermore, the sliding movement of the leaflets 15 against the protuberances 61, 65 spreads the wear of pivoting over extended portions of the leaflet surfaces 41, 43. The leaflets 15 swing open until their upstream surfaces 51 contact the upper protuberances 61 at an angle from the centerline plane between about 10° to about 25°.

When the respective ventricle closes to draw more blood from the atrium, the backflow of blood from the aorta exerts a drag on the greater portions 71 of the leaflets 15 and causes the leaflets to promptly close to prevent any substantial regurgitation of blood. During closing, with the ears 21 of each leaflet 15 guided by the corresponding depressions 23, the upstream surface 41 of each leaflet pivots and slides against the upper protuberances 61, with the eccentric axis being defined between the contact therebetween and shifting towards the straight edge 29.

Preferably each leaflet 15 is stopped in its closed position with its ears 21 spaced slightly from the downstream edges 51 of the depressions 23 and may also be stopped in its open position with the ears spaced slightly from the upstream edges 49. Thus, the stopping force is borne by the protuberances 61, 65, 69 and not by the ears 21, assuring that blood is not squeezed and hemolyzed between the ears and the straight edges 49, 51 of the depressions 23 and that the upstream and downstream edges of the depressions are continually washed by flowing blood.

In addition to their pivoting and stopping functions, the upper and lower protuberances 61, 65 cooperate with the corresponding depressions 23 to retain the leaflets 15 within the valve body 13. In order that the ears 21 may be inserted into the depressions 23, it is necessary that the leaflets 15 and/or the valve body 13 be sufficiently resiliently deformable that the leaflets may be snapped into the body. The inwardly extending protuberances 61, 65, 69 help assure that the leaflets 15 will not snap out of the body 13 when the leaflets are stopped in either their open or closed positions.

The valve 11 is constructed of materials which are thromboresistant and biocompatible and which are sufficiently wear-resistant for permanent implantation into the heart. The valve body 13 may be formed of graphite such as that sold under the trademark POCO graphite and thereafer coated with pyrolytic carbon such as that sold under the trademark PYROLITE which provides a surface with excellent biocompatible and thromboresistant properties. The leaflets 15 may each be formed as a unitary piece of pyrolytic carbon or may be made of a coated substrate.

A typical heart valve body 13 is 5 mm. high, has an outside diameter of 25 mm. and provides a passageway 17 of 23 mm. in diameter. The flat surfaces 27 are spaced 22 mm. from each other and the depressions 23 therein are 1½ mm. deep. The leaflets 15 are 1 mm. thick and have arcuate edges 31 with 11 mm. radii. The straight segments 37 are spaced 21 mm. apart and the ears 21 extend 1½ mm. outward therefrom. The several protuberances 61, 65 and 69 each extend 1½ mm. into the valve body 13.

Illustrated in FIG. 7 is an alternative embodiment of a heart valve 111 which has an annular valve body or housing 113 which carries a valve member 115 in the form of a single disc occluder which opens and closes to control the flow of blood through a central passageway 117 in the direction of the arrow 119 (FIG. 8). A pair of ears 121 extends along opposite ends of an eccentric line across the occluder 115 and interfits with a pair of opposed arcuate depressions 123 in the valve body 113, and the occluder is guided thereby as it swings between its open and closed positions. While the valve 111 can operate in any orientation and is not signficantly affected by gravity, for ease of explanation, the valve is shown and described with the downstream end of the valve facing downward.

The valve body 113 is formed with a peripheral groove 125 about its exterior surface that accommodates a suturing ring (not shown) which facilitates the sewing or suturing of the heart valve 111 to the heart tissue. The passageway 117 through the valve body 113 is generally circular; however, a pair of diametrically opposed flat surfaces 127, in which depressions 123 and several protuberances are formed, interrupt the otherwise circular configuration of the passageway.

The occluder 115, as best seen in FIG. 8, is flat with a uniform thickness throughout and is generally disc-shaped. However, the circulary periphery is interrupted by straight segments 137, from which the ears 121 extend, leaving arcuate edge portions 131a, 131b that lie closely adjacent the arcuate portions of the interior wall in the closed position. The straight segments 137 are spaced apart slightly less than the distance between the opposed flat surfaces 127 of the interior wall and alternately serve as load-bearing surfaces during the swinging movement of the occluder 115. The flat surfaces 127 in the interior wall and corresponding straight segments 137 of the occluder 115 are provided so that those portions of the occluder periphery closely adjacent the centerline plane, i.e., the plane through the valve body centerline perpendicular to the flat surfaces 127, so not bind in more restricted areas of the body 113 as they move away from the centerline plane during opening. The peripheral edge 139 of the occluder 115 is rounded between its upstream face or surface 141 and its downstream face or surface 143 to eliminate sharp corners.

The interengagement of the ears 121 and the complementary depressions 123 serves both to retain the occluder 115 in the valve body 113 and to define the movement of the occluder therein. The ears 121, which extend at opposite ends of an eccentric line from the straight segments 137 of the occluder 115 into the depressions 123, have a generally rectangular configuration. The depressions 123, with which the ears 121 interengage, are generally the shape of arcuate troughs and guide the ears in a generally arcuate pathway. The upstream edges 151, along which the ears 121 lie closely adjacent in the closed position of the occluder 115, are preferably generally perpendicular to the centerline plane, and the arcuate edges 145, 147 extend downstream therefrom and curve away from the centerline plane. The downstream straight edges 149, along which the ears 121 lie closely adjacent in the open position of the occluder 115, are angled from the centerline plane by about 10° to about 25° so that the total angular movement of the ears in the depressions 123 is between about 65° and about 80°.

The arcuate edge 145 of each depression 123 adjacent to the centerline plane and the arcuate edge 147 remote from the centerline plane are not parallel, but diverge toward their downstream ends so that the transverse dimension of each depression increases in a downstream direction. While the length of each ear 121 is sufficient to substantially fill the space between the upstream ends of the adjacent and remote arcuate edges 145, 147 of the corresponding depression 123, the increasing downstream transverse dimension of each depression assures that the depression is well washed by flowing blood to prevent stagnation and resulting clotting therein when the occluder 115 is in non-closed positions.

The arcuate trough-shaped depressions 123 preferably have flat rear walls 153 (FIG. 8) along which the outer ends 154 of the ears 121 locate as they swing between their open and closed positions. The arcuate edges 145, 147 of the depressions 123, which are substantially perpendicular to the flat surfaces 127 and to the rear walls 153, guide the corresponding edges 157, 159 (FIG. 8) of the ears 121. Preferably, the depth of the ears 121 is less than the depth of the depressions 123 so that the occluder 115 is laterally positioned by the flat surfaces 127 of the interior wall and there is no contact between the rear walls 153 of the depressions 123 and the ends 154 of the ears.

The fully open position and fully closed position of the occluder 115 are determined by bumps or protuberances which extend inward of the valve body 113. A downstream or lower protuberance 161 associated with each depression 123 is positioned slightly above (upstream of) and remote from the centerline plane relative to the corner 163 of the corresponding downstream edge 149 and remote arcuate edge 147, and an upstream or upper protuberance 165 associated with each depression is positioned slightly above and remote from the centerline plane relative to the corner 167 of the upstream edge 151 and remote arcuate edge 147.

A protuberance or short lip 169b is positioned on the arcuate portion 133b of the interior wall remote from the depressions 123 to contact the upstream surface 141 of the occluder 115 in its closed position at about the midpoint of its downstream arcuate edge 131b. The lip 169b in certain models may extend around the entire arcuate portion 133b. A protuberance or short lip 169a, optionally included on the valve body 113, is positioned at the midpoint of the arcuate portion 133a of the interior wall adjacent the depressions 123 to contact the downstream surface 143 of the occluder 115 in its closed position at about the midpoint of its upstream arcuate edge 131a.

In its closed position, the occluder 115 seats with its upstream surface 141 abutting the corresponding upper protuberances 165 and midpoint protuberances 169a, 169b in a plane substantially perpendicular to the centerline plane. The upper protuberances 165 and midpoint protuberances 169 are so positioned that in the closed position, the downstream surface 143 of the occluder 115 lies closely adjacent the corresponding lower bumps or protuberances 161. In its open position, the occluder 115 is positioned with its upstream surface 141 abutting the upper protuberances 165 and its downstream surface 143 abutting the lower protuberances 161 and with its ears 121 abutting or lying closely adjacent the downstream straight edges 149.

The upper and lower protuberances 165, 161 serve as surfaces against which the occluder 115 slides and pivots during closing and opening, respectively. An eccentric axis is defined between the contact points of the occluder 115 and the corresponding pair of protuberances 161 or 165 during opening and closing.

For a valve 111 in the aortic position, during the pumping stroke of the heart, the occluder 115 is pushed into contact with the lower protuberances 161 and out of contact with the upper protuberances 165. The force differential resulting from blood pressure from the ventricle against the greater portion 171 of the occluder 115, relative to the lower protuberances 161, swings the occluder in its downstream direction with its downstream arcuate edge 131b moving in a wide arc. During opening, the ears 121 of the occluder 115 are guided by the arcuate depressions 123 as the downstream surface 143 slides and pivots against the lower protuberances 161. The arcuate depressions 123 are elongated and do not have a radius of curvature that coincides with the pivotal axis of the occluder 115. Thus, during opening movement, there is a slight downstream translation of the occluder 115, with the occluder sliding as well as pivoting against the lower protuberances 161 so that the pivotal axis, defined by the contact of the lower protuberances and the downstream surface 143, continuously shifts toward the upstream edge 131a. The occluder 115 swing open until its upstream surface 141 again contacts the upper protuberances 165 with the occluder disposed in the valve body 113 at an angle from the centerline plane between about 10° to about 25°.

When the respective ventricle closes to draw more blood from the atriun, the backflow of blood from the aorta exerts a drag on the major portions 171 of the occluder 115, relative to the upper protuberances 165, and causes the occluder to promptly close to prevent any substantial regurgitation of blood. During closing, with the ears 121 of the occluder 115 guided by the corresponding depressions 123, the upstream surface 141 of the occluder pivots and slides against the upper protuberances 165, with the eccentric axis being defined between the contact therebetween and shifting towards the downstream arcuate edge 133b. The translational movement of the ears 121 within the depressions 123 and the relocation of the occluder 115 relative to the protuberances 161, 165 results in a continual sliding of the contact surfaces which serves to prevent blood from stagnating in and clotting in the restricted areas in the depressions and around the protuberances. Furthermore, the sliding movement of the occluder 115 against the protuberances 161, 165 spreads the wear of pivoting over extended portions of the occluder surfaces 141, 143.

Preferably the occluder 115 is stopped in its closed position with its ears 121 spaced slightly from the upstream edges 151 of the depressions 123 and may also be stopped in its open position with the ears spaced slightly from the downstream edges 149. Thus, the stopping force is borne by the protuberances 169, 165, 161 and not by the ears, assuring that blood is not squeezed and hemolyzed between the ears and the straight edges of the depressions and that the upstream and downstream edges of the depressions are continually washed by flowing blood.

In addition to their pivoting and stopping functions, the upper and lower protuberances 165, 161 cooperate with the corresponding depressions 123 to retain the occluder 115 within the valve body 113. In order that the ears 121 may be inserted into the depressions 123, it is necessary that the occluder 115 and/or the valve body 113 be sufficiently resiliently deformable that the occluder may be snapped into the body. The inwardly extending protuberances 161, 165, 169 help assure that the occluder 115 will not snap out of the body 113 when the occluder is stopped in either its open or closed positions.

Illustrated in FIG. 9 is an alternative embodiment of a single disc occluder heart valve 211 in which the occluder 215 has an arcuate cross section and a generally uniform thickness. The occluder 215 has a configuration generally that of a portion of a tube, such as a hollow right circular or elliptical cylinder. The preferred occluder configuration is generally a portion of a hollow right elliptical cylinder with the minor elliptical axis 210 (FIG. 12) intersecting the straight centerline 212 of the occluder 215, and the occluder 215 is disposed in the valve body 213 with its convex surface 241 facing upstream. The elliptical cross-sectional configuration provides a region 220 along its centerline 212 which is fairly flat relative to the edge regions 219. The length of the major elliptical axis 228 of the tube from which the occluder 215 may be shaped is preferably between about 120% and about 200% of the passageway diameter, and the length of the minor elliptical axis 210 is between about 50% and about 170% of the passageway diameter. The depth X (FIG. 12) of the concave surface as measured from the base of the occluder 215 to the centerline of the concave surface 243 should be between about 15% and about 30% of the passageway diameter.

The occluder 215 is oriented within the valve body 213 so that it seats in the closed position with its centerline 212 at an angle of from 65° to 90° to the passageway centerline. In the illustrated embodiment, the downstream edge 231b and upstream edge 231a have the same general shape, i.e., the intersection between the elliptical hollow cylinder that defines the body of the occuluder 215 and the right circular cylinder that defines the interior wall 233 of the passageway 217.

The occluder 215 is formed with flat lateral edge segments 237 which alternately abut the diametrically opposite flat surfaces 227 on the interior wall of the valve body and which serve as bearing surfaces during the pivoting movement of the occluder. Depressions 223 in the flat surfaces 227 in combination with protuberances 261, 265 that extend generally radially inward from the flat surfaces 227 guide the occluder. A pair of generally rectangular-shaped ears 221 extend from the flat segments 237 of the occluder 215 and are received in the guiding depressions.

The action of the occluder 215 is similar to the action of occluder 115 of the heart valve 111, described hereinabove in reference to FIGS. 7-8. The occluder 215 is guided for pivotal and translational movement during opening and closing by the movement of the ears 221 in the elongated depressions 223. The occluder stops in the closed position (FIG. 10) with its upstream surface 241 in contact with the two upstream protuberances 265 and a third protuberance 269 on the opposite side of the valve centerline. In the open position, the occluder 215 stops with its upstream surface 241 still in contact with the two upstream protuberances 265 and with its downstream surface 243 abutting the downstream protuberances 261. The centerline 212 of the occluder in the open position forms an angle of from about 10° to about 25° with the passageway centerline.

When the occluder 215 is in the open position, it defines a minor passageway portion 254 along its concave downstream surface 243 (FIG. 9) and a major portion 256 along its convex surface 241. Because the concave downstream surface 243 enlarges the minor passageway portion 254, the particular arcuate cross section of the occluder 215 tends to equalize the passageway portions 254, 256. This equalization assures that the area of the minor passageway portion is not so restricted that little flow of blood will take place, thus increasing the overall performance of the valve 211.

Illustrated in FIGS. 13-16 is a still further alternative embodiment of a heart valve 311 which features a depression-protuberance arrangement resembling that illustrated in FIGS. 9-12. The heart valve 311 has a dome-shaped occluder 315 having a convex-concave configuration generally that of a sector of a hollow sphere. It should be appreciated that different occluder configurations, i.e., flat, tubular or dome-shaped, may be used with various of the depression-protuberance arrangements illustrated herein.

The occluder 315 has a planer periphery including a downstream arcuate edge 324 and an upstream arcuate edge 326, which are generally semicircular and proportioned to lie closely adjacent arcuate portions of the interior wall in the closed position to block blood flow through the valve passageway 317, and a pair of straight segments 337, which lie closely adjacent opposed flat surfaces 327 of the interior wall and alternately serve as bearing surfaces when the occluder 315 pivots. The movement of the occluder is guided by a pair of opposed, arcuate, trough-shaped depressions 323, which are formed in the flat surfaces 327, together with upstream rounded protuberances 361 and downstream rounded protuberances 365, which are located between the centerline plane of the valve and the depressions 323. A pair of ears 321 extend from the straight segments 337 of the occluder 315 and are received in the arcuate depressions 323.

The arcuate depressions 323 terminate at downstream walls 351 which, in the illustrated embodiment, are generally perpendicular to the centerline plane. Arcuate depression walls 345 and 347 curve upstream from the downstream wall 351 toward the centerline plane. The arcuate walls 345, 347 diverge in the upstream direction so that the transverse dimension of each depression 323 increases in an upstream direction, providing for washing of the depressions by blood flowing through the valve. Upstream straight walls 349 of the depression 323 may serve as stops for the ears 321 in the open position.

The movement of the occluder 315 between its open and closed positions is defined by the interengagement of the ears 321 within the depressions 323 and by the upstream and downstream protuberances associated with the depressions. The downstream protuberances 365 provide pivot points for the periphery of the occluder 315 as it shifts to the open position. The upstream protuberances 361 similarly provide pivot points in contact with the upstream surface 341 as the occluder 315 shifts to its closed position. The arcuate walls 345, 347 of the depressions do not have a constant radius of curvature but instead guide the occluder 315 in translational as well as pivotal movement as it shifts between its open and closed positions.

For a valve 311 in the aortic position during the beginning of the pumping stroke of the heart, the differential force resulting from blood pressure in the ventricle against the greater portion 371 of the occluder 315

(lying to the right of the downstream protuberances 365 in FIG. 14), shifts the occluder to its open position. The occluder pivots about the downstream protuberances 365, with the downstream surface 343 of its periphery in sliding contact therewith. In this shifting, the occluder is guided for pivotal and translational movement by the travel of the ears 321 along the arcuate walls 347 of the depressions. The occluder continues shifting to its open position until its upstream surface 341 contacts the upstream protuberances 361, stopping its movement with the ears 321 adjacent or in contact with the upstream walls 349 of the depressions.

When the respective ventricle expands to draw more blood from the atrium, backflow of blood from the aorta exerts a drag on the major portion 371 of the occluder causing it to begin to shift toward the closed position, with its upstream surface 343 in sliding contact with the upstream rounded protuberances 361 that serve as pivot points. The occluder is stopped in its closed position with its ears 321 against the downstream walls 351 and with its upstream surface 341 in contact with the upstream protuberances 361 and some auxiliary stops 355 and 356. In the illustrated valve, a pair of rounded stops 356 protrude from the flat surfaces 327 on the opposite side of the centerline plane from the upstream protuberances 361, and a single rounded stop 355 is located in the arcuate wall of the valve body 313 midway between the stops 356.

The illustrated arcuate sections 324, 326 of the occluder periphery are segments of circles, but would be elliptical if the occluder 315 were designed to seat in the closed position with its periphery in a plane at an angle of less than 90° to the passageway centerline.

The dome-shaped convex-concave occluder 315 preferably has a generally uniform thickness and is disposed in the valve body 313 with its convex surface 341 facing upstream in the closed position of the heart valve. In its open position, the occluder 315 defines a major passageway portion 357 (FIG. 13) along its upstream convex surface 341 and a minor passageway portion 354 along its downstream concave surface 343. It is preferred that the height Y (FIG. 16) of the dome, as measured from its base, i.e., the plane of its periphery, to the apex of its concave surface 343, be about 15 to about 30 percent of the passageway diameter.

Illustrated in FIG. 17 is a further alternative embodiment of a bileaflet heart valve 411 in which each of the leaflets 415 has a convex-concave configuration generally that of one-half of a sector of a hollow sphere. The convex surface 451 of each of the leaflets faces upstream, and the leaflets in their open position provide a generally ellipitical central region between their concave downstream surfaces 447 with good blood flow characteristics.

Depressions 435 formed in diametrically opposite flat regions 427 of the valve body 413 interengage with ears 421 extending outward from the flat peripheral segments 437 of the leaflets to guide the leaflets on curving pathways as they shift between their open and closed positions.

Each of the leaflets 415 is stopped in its open position with its convex upstream surface 451 in contact with a pair of opposed, rounded, upstream protuberances 465 associated with the corresponding guiding depressions 423 and with its downstream surface 443 in contact with downstream protuberances 461. Each of the leaflets is stopped in its closed position with its upstream convex surface 441 in contact with the upstream protuberances 465 and with its arcuate peripheral edge 431 in contact with a ledge or lip 464 formed in the arcuate interior wall 433 of the valve body. Each of the leaflets is stopped in its open position with its arcuate peripheral edge 431 in a plane which meets the passageway centerline at an angle of between about 10° and about 25° and in its closed position in a plane at an angle of between about 65° and 90°. When, as illustrated, the leaflets 415 seat in their closed positions, the peripheral edge 431 of each has the elliptical shape defined by the intersection of the plane of the periphery and the cylindrical interior surface of the valve body.

Illustrated in FIG. 18 is a further alternative embodiment of a bileaflet heart valve 511 in which each of the leaflets 515 has a convex-concave configuration generally that of a sector or portion of a right cylindrical tube. The axis of the leaflet 515 should be understood to mean the axis of this tube. The leaflets 515 have flat lateral edge sections 537 from which ears 521 extend in opposite directions. The ears are received in depressions 523 formed in opposite flat wall portions 527 of the interior of the valve body. The depressions 523 guide the leaflets in shifting between their open and closed positions and extend partially into upstanding standards 536, which project from the upstream surface of the otherwise annular valve body 513.

The leaflets 515 are stopped in the open position with their convex upstream surfaces 541 in contact with rounded upstream protuberances 565 associated with the corresponding depressions 523 and with their downstream surfaces 543 adjacent the flat sections 537 in contact with downstream protuberances 561. In the closed position, the leaflets are stopped with their convex upstream surfaces 541 still in contact with the upstream protuberances 565 and with their peripheral arcuate edges 531 in contact with the arcuate interior wall 533 of the valve body.

The convex-concave configuration of the leaflets 515 provides a generally elliptical central passageway with good blood flow characteristics past the facing concave surfaces 543 of the leaflets in the open position. The standards 536, which project in the upstream direction, permit the leaflets to seat in their closed position with their axes at an angle of substantially less than 90° relative to the centerline of the valve body, and auxiliary protuberances or lips can be optionally omitted because the major edges 531 of the leaflets bear tightly against the arcuate interior wall 533. Preferably the leaflets, in heart valves having standards 536 extending upstream, seat in their closed position with their axes inclined toward the passageway centerline at an angle of between about 65° and about 70°. Because in the open position, the axes of the leaflets are inclined toward the passageway centerline at an angle of between about 10° and about 25°, the distance that the leaflets are required to shift between their open and closed positions is thereby small, i.e., only between about 45° and about 60°. The small shifting movement of the leaflets required to close the valve 511 hastens closing and reduces backflow through the valve.

Illustrated in FIG. 19 is a further alternative embodiment of a heart valve 611 having a single occluder 615 that has a concave-convex configuration generally that of a sector of a hollow sphere with its concave surface 641 facing upstream. The interengagement of opposed ears 621 that project from flat lateral surfaces 622 with a pair of elongated depressions 623 helps to guide the occluder in shifting between its open and closed positions. The occluder 615 is stopped in its open position by contact with pairs of upstream and downstream protuberances 665, 661. In the closed position, the occluder is in contact with the upstream protuberances 665, and its arcuate peripheral edge 631, remote from this region of contact, seats along a lip 669 formed in the arcuate interior wall 633 of the valve body. In the closed position, the illustrated occluder 615 seats in the valve body 613 with the plane of its periphery at an angle of less than 90° from the centerline of the valve passageway, thus reducing the angular distance the occluder pivots.

Many advantages of the heart valves should now be more fully appreciated. The low profile of the heart valves and the large generally unobstructed passageway contribute to excellent flow of blood therethrough. Almost all surfaces are fully exposed to flowing blood which washes the surfaces and prevents stagnation and clotting. The increasing transverse dimensions of the depressions permit flowing blood to wash the most restricted area, i.e., between the ears and the depressions, and, in this regard, the configuration of the depressions which results in translational movement of the valve member(s) also causes some sliding of the ears along the depression surfaces to continually clean these surfaces. Because the shifting valve member(s) are generally in contact with the valve body at least one set of protuberances as well as along the depressions, and because the contact points are continually changing, the force between the valve member(s) and the valve body is well distributed, and wear on the heart valves is minimized. Similarly, the distribution of the opening and closing forces over several surfaces cushions the impact so that no significant hemolysis occurs. The design of the heart valves is simple so that they may be easily manufactured and reproduced according to exacting standards to provide lifelong trouble-free use.

While the invention has been described in terms of certain preferred embodiments, modifications obvious to one of the ordinary skill in the art may be made without departing from the scope of the invention. For example, the ears may be arcuate rather than rectangular, in which case the rear walls of the depressions would be correspondingly arcuate.

A number of embodiments have been shown and described which are well representative of ear-guided heart valves of the present invention. These embodiments incorporate a variety of features which are incorporated according to the requirements of the patient and manufacturing considerations into a variety of modifications or permutations. It will be understood that the various permutations, which arise from rearranging the various features that have been described herein in reference to the illustrated embodiments, are within the scope of the invention.

Various features of the invention are set forth in the following claims.

What is claimed:

1. A heart valve prosthesis for allowing normal blood flow therethrough from upstream to downstream including:
    a generally annular valve body having an interior wall which defines a central passageway for blood flow therethrough,
    occluder means for blocking the reverse flow of blood through said passageway,
    ears extending from opposite locations on the periphery of said occluder means,
    complementary depressions formed in said interior wall of said valve body which are proportioned to receive said ears and to guide said ears along a curving path as said occluder means moves between closed and open positions,
    stop means in said annular valve body against which the upstream face of said occluder means abuts in the closed position,
    first and second bump means protruding from said interior wall and being associated with each of said depressions, said first bump means being located downstream of said occluder means and said second bump means being located upstream of said occluder means in said closed position, said first bump means being in contact with the downstream face of said occluder means during moving to said open position and determining the orientation of said occluder means in the fully open position, and
    the shape of said depressions being such to, in cooperation with said bump means, guide said occluder means in both pivotal and translational movement between said closed and open positions, whereby said downstream face of said occluder means slides against said first bump means during opening of said occluder means.

2. A heart valve in accordance with claim 1 wherein said depressions are formed in substantially flat surfaces formed at diametrically opposite locations in said interior wall of said valve body, and said occluder means has flat lateral sides from which said ears extend.

3. A heart valve in accordance with claim 1 wherein said depressions are curving troughs having flat rear walls and substantially perpendicular sidewalls, wherein the transverse dimension of said curving troughs increases in the direction which said ears travel as said occluder means moves to its open position.

4. A heart valve prosthesis according to claim 1 wherein said occluder means has a convex upstream face and a concave downstream face.

5. A heart valve prosthesis according to claim 1 having upstanding standards into which said depressions extend.

6. A heart valve prosthesis according to claim 5 wherein said standards extend from said valve body in an upstream direction.

7. A heart valve in accordance with claim 1 wherein said occluder means is a unitary occluder.

8. A heart valve in accordance with claim 7 wherein said stop means includes said second bump means and also includes an auxiliary protuberance extending inward from said valve body on the other side of the centerline plane from said second bump means.

9. A heart valve in accordance with claim 7 wherein said second bump means is positioned to engage in sliding contact with the upstream face of said occluder during pivoting and translational movement to the closed position.

10. A heart valve in accordance with claim 7 wherein said passageway is generally circular, said occluder is generally circular and lies in a plane which meets to the centerline of said valve body in its closed position at an angle of between about 65° and about 90°.

11. A heart valve in accordance with claim 7 wherein said occluder is generally a sector of a tube of curved cross section, said occluder having a generally straight centerline with said ears extending from lateral edges on opposite sides of said centerline.

12. A heart valve according to claim 11 wherein said occluder is generally a sector of a hollow right elliptical cylinder, the length of the major elliptical axis being between about 120 and about 200 percent the diameter of said passageway and the length of the minor elliptical axis being between about 50 and about 170 percent of the diameter of said passageway.

13. A heart valve in accordance with claim 7 wherein said occluder is dome-shaped having a concave and a convex face.

14. A heart valve in accordance with claim 7 wherein said first and second bump means are disposed remote from the centerline plane relative to said depressions, and said depressions provide a downstream pathway for said ears as said occluder moves to its open position.

15. A heart valve in accordance with claim 7 wherein said first and second bump means are located between the centerline plane and said depressions, and said depressions provide an upstream pathway for said ears as said occluder moves to its open position.

16. A heart valve in accordance with claim 1 wherein said occluder means includes a pair of leaflets having arcuate major edges and flat minor edges which lie closely adjacent each other in the closed position.

17. A heart valve in accordance with claim 16 wherein said depressions are curving troughs having a flat rear wall and substantially perpendicular sidewalls, wherein the transverse dimension of said curving troughs increases in an upstream direction.

18. A heart valve in accordance with claim 16 wherein said stop means includes a pair of protuberances at diametrically opposite locations on said valve body where they contact said leaflets at about the midpoints of said major arcuate edges and also includes said second bump means.

19. A heart valve in accordance with claim 16 wherein each of said second bump means associated with said depressions is positioned to engage in sliding contact with the upstream face of one of said leaflets during pivoting and translational movement to the closed position.

20. A heart valve according to claim 16 wherein said leaflets each have a concave-convex configuration generally in the shape of a sector of a hollow right cylindrical tube.

21. A heart valve prosthesis for allowing blood flow therethrough in a specific direction including
a generally annular valve body having an interior surface defining a central passageway for blood flow therethrough,
a single occluder having a concave downstream face and a convex upstream face, the depth of the concave face being between about 15 and 30 percent of the passageway diameter,
a pair of ears formed on opposite generally central locations on the periphery of said occluder, said ears defining a pivot axis that is eccentric and that divides said occluder into a greater portion and a lesser portion,
a pair of complementary depressions in said interior surface which are proportioned to interfit with said ears for guiding said occluder in pivoting action between an open position where said greater portion of said occluder extends downstream from said eccentric axis and a closed position, said occluder in said open position dividing said passageway into a major passageway portion and a minor passageway portion, the concave-convex configuration of said occluder tending to equalize the areas of said passageway portions, the shape of said depressions being such to guide said occluder along a curving path during shifting between said open and closed positions that creates both pivotal and translational movement,
first means formed in said annular valve body for engaging said upstream face of said occluder and providing a stop in the closed position, and
second means in said annular valve body for engaging said downstream face of said occluder and providing a stop in the open position.

22. A heart valve in accordance with claim 21 wherein said occluder includes a sector of a tube of curved cross section having a generally straight centerline that is perpendicular to the pivotal axis.

23. A heart valve prosthesis for allowing blood flow therethrough in a specific direction including
a generally annular valve body having an interior surface defining a central passageway for blood flow therethrough,
a single occluder that includes a sector of a hollow right elliptical cylinder, having a concave downstream face, a convex upstream face and a generally straight centerline, the depth of the concave surface being between about 15 and about 30 percent of the passageway diameter, the length of a major elliptical axis being between about 120 and about 200 percent of the diameter of said passageway and the length of the minor elliptical axis being between about 50 and about 170 percent of the length of the diameter of said passageway,
a pair of ears formed on opposite locations in the periphery of said occluder,
a pair of complementary depressions in said interior surface which depressions are proportioned to receive said ears for guiding said occluder in pivoting action between open and closed positions, the shape of said depressions being such to guide said occluder along a curving path during shifting between said open and closed positions that creates both pivotal and translational movement,
first means formed in said annular valve body for engaging said upstream face of said occluder and providing a stop in the closed position, and
second means in said annular valve body for engaging said downstream face of said occluder and providing a stop in the open position.

24. A heart valve in accordance with claim 21 wherein said occluder is dome-shaped.

* * * * *